(12) United States Patent
Haider et al.

(10) Patent No.: US 8,157,768 B2
(45) Date of Patent: Apr. 17, 2012

(54) DISPOSABLE INJECTION DEVICE

(75) Inventors: M. Ishaq Haider, Morrisville, NC (US);
Timothy Erskine, Sandy, UT (US);
Ronald J. Pettis, Cary, NC (US)

(73) Assignee: Becton Dickinson and Company,
Franklin Lakes, NJ (US)

( * ) Notice: Subject to any disclaimer, the term of this patent is extended or adjusted under 35 U.S.C. 154(b) by 0 days.

(21) Appl. No.: 12/980,574

(22) Filed: Dec. 29, 2010

(65) Prior Publication Data
US 2011/0098641 A1    Apr. 28, 2011

Related U.S. Application Data

(62) Division of application No. 11/769,214, filed on Jun. 27, 2007, now Pat. No. 7,905,866, which is a division of application No. 10/337,413, filed on Jan. 7, 2003, now Pat. No. 7,252,651.

(51) Int. Cl.
*A61M 5/00* (2006.01)
*A61M 5/32* (2006.01)

(52) U.S. Cl. .......................... 604/110; 604/193; 604/198

(58) Field of Classification Search .................. 604/110, 604/111, 117, 130, 135–139, 181, 193, 198, 604/201, 203, 232
See application file for complete search history.

(56) References Cited

U.S. PATENT DOCUMENTS

| | | | |
|---|---|---|---|
| 2,752,918 A | 7/1956 | Uytenbogaart | |
| 3,797,489 A | 3/1974 | Sarnoff | |
| 4,188,950 A | 2/1980 | Wardlaw | |
| 4,214,584 A | 7/1980 | Smirnov et al. | |
| 4,227,528 A | 10/1980 | Wardlaw | |
| 4,258,713 A | 3/1981 | Wardlaw | |
| 4,340,048 A | 7/1982 | Eckenhoff | |
| 4,378,015 A | 3/1983 | Wardlaw | |
| 4,484,910 A | 11/1984 | Sarnoff et al. | |
| 4,565,543 A | 1/1986 | Bekkering et al. | |
| 4,734,092 A | 3/1988 | Millerd | |
| 4,753,651 A | 6/1988 | Eckenhoff | |
| 4,781,688 A | 11/1988 | Thoma et al. | |
| 4,822,340 A | 4/1989 | Kamstra | |
| 4,886,499 A | 12/1989 | Cirelli et al. | |
| 4,894,054 A | 1/1990 | Miskinyar | |
| 4,894,055 A * | 1/1990 | Sudnak ........................ 604/198 |
| 4,902,279 A * | 2/1990 | Schmidtz et al. ............. 604/134 |

(Continued)

FOREIGN PATENT DOCUMENTS

DE    2054 037    5/1972

(Continued)

*Primary Examiner* — Kevin C Sirmons
*Assistant Examiner* — Andrew Gilbert
(74) *Attorney, Agent, or Firm* — Hoffman & Baron, LLP

(57) ABSTRACT

An injection device is provided. The device includes a housing having a first end defining a first opening. A plunger is received within the first opening of the housing to move between first and second positions. A cartridge is disposed in the housing and has an interior serving as a reservoir for a drug. A delivery needle is disposed within the housing and is in fluid communication with the reservoir via an interruptible fluid channel. A locking mechanism is disposed in the housing. In the first position of the plunger the delivery needle is enclosed by the plunger and in the second position of the plunger the delivery needle is placed in an injection position and the plunger activates the locking mechanism whereby when the plunger returns to the first position the locking mechanism prevents the needle from being placed in the injection position.

19 Claims, 6 Drawing Sheets

U.S. PATENT DOCUMENTS

| | | | |
|---|---|---|---|
| 4,936,830 A | 6/1990 | Verlier | |
| 4,968,302 A | 11/1990 | Schluter et al. | |
| 4,983,164 A | 1/1991 | Hook et al. | |
| 5,085,642 A | 2/1992 | Sarnoff et al. | |
| 5,092,842 A | 3/1992 | Bechtold et al. | |
| 5,092,843 A | 3/1992 | Monroe et al. | |
| 5,102,393 A | 4/1992 | Sarnoff et al. | |
| 5,104,384 A | 4/1992 | Parry | |
| 5,114,404 A | 5/1992 | Paxton et al. | |
| 5,137,516 A * | 8/1992 | Rand et al. | 604/136 |
| 5,176,643 A | 1/1993 | Kramer et al. | |
| 5,273,544 A | 12/1993 | van der Wal | |
| 5,307,953 A | 5/1994 | Regan | |
| 5,320,609 A | 6/1994 | Haber et al. | |
| 5,334,144 A | 8/1994 | Alchas et al. | |
| 5,358,489 A | 10/1994 | Wyrick | |
| 5,391,151 A | 2/1995 | Wilmot | |
| 5,425,715 A | 6/1995 | Dalling et al. | |
| 5,472,430 A | 12/1995 | Vaillancourt et al. | |
| 5,478,316 A | 12/1995 | Bitdinger et al. | |
| 5,514,097 A | 5/1996 | Knauer | |
| 5,527,287 A | 6/1996 | Miskinyar | |
| 5,540,664 A | 7/1996 | Wyrick | |
| 5,567,160 A | 10/1996 | Massino | |
| 5,569,192 A | 10/1996 | van der Wal | |
| 5,616,128 A | 4/1997 | Meyer | |
| 5,616,132 A | 4/1997 | Newman | |
| 5,656,032 A | 8/1997 | Kriesel et al. | |
| 5,658,259 A * | 8/1997 | Pearson et al. | 604/232 |
| 5,681,291 A * | 10/1997 | Galli | 604/192 |
| 5,709,662 A | 1/1998 | Olive et al. | |
| 5,813,570 A | 9/1998 | Fuchs et al. | |
| 5,858,001 A * | 1/1999 | Tsals et al. | 604/135 |
| 5,873,856 A | 2/1999 | Hjertman et al. | |
| 5,957,895 A | 9/1999 | Sage et al. | |
| 6,045,534 A | 4/2000 | Jacobsen et al. | |
| 6,099,503 A * | 8/2000 | Stradella | 604/135 |
| 6,099,504 A | 8/2000 | Gross et al. | |
| 6,149,626 A | 11/2000 | Bachynsky et al. | |
| 6,186,980 B1 | 2/2001 | Brunel | |
| 6,203,530 B1 | 3/2001 | Stewart, Sr. | |
| 6,210,369 B1 * | 4/2001 | Wilmot et al. | 604/157 |
| 6,213,977 B1 | 4/2001 | Hjertman et al. | |
| 6,270,479 B1 | 8/2001 | Bergens et al. | |
| 6,280,421 B1 * | 8/2001 | Kirchhofer et al. | 604/218 |
| 6,319,233 B1 | 11/2001 | Jansen et al. | |
| 6,371,939 B2 | 4/2002 | Bergens et al. | |
| 6,391,003 B1 * | 5/2002 | Lesch, Jr. | 604/110 |
| 6,406,455 B1 | 6/2002 | Willis et al. | |
| 6,428,528 B2 | 8/2002 | Sadowski et al. | |
| 6,443,151 B1 | 9/2002 | Ruskewicz | |
| 6,494,865 B1 | 12/2002 | Alchas | |
| 6,544,234 B1 | 4/2003 | Gabriel | |
| 6,565,553 B2 | 5/2003 | Sadowski et al. | |
| 6,569,143 B2 | 5/2003 | Alchas et al. | |
| 6,575,939 B1 | 6/2003 | Brunel | |
| 6,585,702 B1 | 7/2003 | Brunel | |
| 6,616,627 B2 | 9/2003 | Willis et al. | |
| 6,641,560 B1 | 11/2003 | Bechtold et al. | |
| 6,673,038 B2 | 1/2004 | Weston | |
| 6,679,864 B2 | 1/2004 | Gagnieux et al. | |
| 6,681,810 B2 | 1/2004 | Weston | |
| 6,682,504 B2 | 1/2004 | Nelson et al. | |
| 6,685,676 B2 | 2/2004 | Jansen et al. | |
| 6,689,108 B2 | 2/2004 | Lavi et al. | |
| 6,689,118 B2 | 2/2004 | Alchas et al. | |
| 6,692,469 B1 | 2/2004 | Weekes et al. | |
| 6,719,730 B2 | 4/2004 | Jansen et al. | |
| 6,746,429 B2 | 6/2004 | Sadowski et al. | |
| 6,752,798 B2 | 6/2004 | McWethy et al. | |
| 7,252,651 B2 * | 8/2007 | Haider et al. | 604/193 |
| 7,641,649 B2 | 1/2010 | Moberg et al. | |
| 7,905,866 B2 * | 3/2011 | Haider et al. | 604/193 |
| 2002/0045866 A1 | 4/2002 | Sadowski et al. | |
| 2003/0106824 A1 | 6/2003 | Wilmot et al. | |
| 2003/0187395 A1 | 10/2003 | Gabel et al. | |
| 2005/0165381 A1 | 7/2005 | Norrie et al. | |

FOREIGN PATENT DOCUMENTS

| | | |
|---|---|---|
| EP | 0 144 625 A2 | 6/1985 |
| EP | 0 577 448 A1 | 1/1994 |
| EP | 0 824 922 A1 | 2/1998 |
| FR | 2 770 404 A1 | 5/1999 |
| WO | 94/11041 A1 | 5/1994 |
| WO | 95/13838 A1 | 5/1995 |
| WO | 97/21457 A1 | 6/1997 |
| WO | 01/72354 A2 | 10/2001 |
| WO | 02/47746 A1 | 6/2002 |

* cited by examiner

DISPOSABLE INJECTION DEVICE

CROSS-REFERENCE TO RELATED APPLICATION

This application is a division of U.S. application Ser. No. 11/769,214 filed Jun. 27, 2007, now U.S. Pat. No. 7,905,866, which is a division of U.S. application Ser. No. 10/337,413, filed Jan. 7, 2003, now U.S. Pat. No. 7,252,651, the entire contents of which are incorporated by reference herein.

BACKGROUND OF THE INVENTION

1. Field of the Invention

The present invention relates generally to a device for delivering a therapeutic preparation into the body of a patient by injection into or through the patient's skin. More particularly, the invention relates to an automatic injection device that incorporates a self-emptying reservoir.

2. Related Art

The conventional method of administration of a drug to a subject is by injection using a hypodermic syringe. A number of difficulties associated with these syringes have led to attempts to derive more advantageous drug delivery devices. Syringes are not generally advocated for use in self administration by patients because of the dangers of embolisms arising from the introduction of air bubbles into the bloodstream, incorrect dosing, and the accidental infection of third parties after use of the syringe. In any event, syringes cannot be used by children or by many elderly patients, and the use of syringes is very traumatic for the large number of people who are needlephobic to a greater or lesser extent.

Various types of automatic injection devices have been developed to allow drug solutions and other liquid therapeutic preparations to be administered by untrained personnel. In trying to provide improved injection devices, a number of inventors have focused on the provision of a pre-filled syringe or a pre-filled ampoule for use in a syringe, as these devices can be useful in addressing the problems of incorrect dosage or incorrect filling of syringes. Furthermore, some syringes have been provided with expelling means which automatically deliver the drug from the syringe body or ampoule, rather than relying on a conventional syringe mechanism which can be difficult to manipulate in a smooth uniform fashion with one hand.

Generally, these devices include some type of automatic needle-driving mechanism (usually of the spring-loaded type) that can be triggered by the user. Examples of such devices may be found in U.S. Pat. Nos. 4,188,950, 4,196,732, 4,258,713, 4,227,528, and 4,378,015 all to Stephen C. Wardlaw. Still further examples can be found in U.S. Pat. No. 4,214,584 to Smirnov et al., U.S. Pat. Nos. 4,894,054 and 5,527,287, both to Miskinyar, and U.S. Pat. No. 5,616,132, to Newman. In order to start the flow of the liquid therapeutic preparation when the needle is injected, the devices disclosed in the aforementioned patents generally employ movable ampoules, pistons or other complex arrangements which are somewhat difficult to manufacture.

Another class of devices includes those which are capable of gradually infusing a liquid therapeutic preparation into the skin of a patient. In some cases, these devices are small enough (both in height and in overall size) to allow them to be "worn" by an ambulatory patient while the liquid therapeutic preparation is being infused into the patient. Examples of devices which fall in to this class include those disclosed in U.S. Pat. Nos. 4,340,048 and 4,753,651, both to Eckenhoff, U.S. Pat. No. 4,734,092, to Miller, U.S. Pat. No. 4,781,688, to Thoma et al., U.S. Pat. No. 4,886,499, to Cirelli et al., U.S. Pat. No. 5,656,032, to Kriesel et al. and PCT Publication Nos. WO 95/13838 and WO 97/21457, both to Elan Medical Technologies, Ltd.

Unfortunately, most of the automatic infusion devices disclosed in the prior art are fairly complex in design and, as a result, cannot be made as small and inexpensive as might be desired. Generally, the complexity of these devices results from three factors. One factor is the need for a pump or other type of discharge mechanism to force the liquid therapeutic preparation to flow out of the reservoir and into the injection or infusion needle. Another factor is the need for some type of valve or flow control mechanism to cause the liquid therapeutic preparation to begin to flow at the proper time. A third factor, which applies to those devices that are designed to inject the infusion needle into the patient automatically, is the need for a suitable injection mechanism that can be triggered by the user. The structures required to perform these functions add size and complexity to the infusion device, making it larger than desired and relatively expensive to manufacture.

Accordingly, a need exists for a drug delivery devise that is capable of delivering a pre-set dosage of drug to a subject; is suitable for use in self-administration by patients (including young patients and elderly patients); does not require the patient to consciously insert a needle into the skin; includes a safety mechanism to prevent re-use of the needle; and has a simple construction. Further objects and advantages of the invention will become apparent from the description given below.

BRIEF SUMMARY OF THE INVENTION

In an exemplary embodiment of the invention, a bolus injection device is provided. The injection device comprises a housing having a first end defining a first opening. A plunger is slidably received within the first opening of the housing to move between first and second positions. The plunger has a bottom surface adapted to be brought into contact with the skin of a subject and prongs extending into the shell. In the first position, the plunger at least partially extends out of the first opening. A resilient member biases the plunger into its first position. A cartridge is disposed in the housing and has an interior serving as a reservoir for a drug. The cartridge is moveable between first and second positions. A delivery needle is disposed within the housing. The delivery needle is out of fluid communication with the reservoir when the cartridge is in its first position and in fluid communication with the reservoir when the cartridge is in its second position, wherein the plunger is moved against the force of the resilient member to its second position to expose the delivery needle to the skin of the subject and to actuate movement of the cartridge from its first position to its second position.

In another embodiment of the invention, an automatic injection device is provided. The device comprises a shell having a longitudinal axis and defines first and second openings on opposite sides of the longitudinal axis. A plunger is slidably received within the first opening of the housing to move between first and second positions. The plunger has a bottom surface adapted to be brought into contact with the skin of a subject and prongs extending into the shell. In the first position, the plunger at least partially extends out of the first opening. A resilient member biases the plunger to the first position. A cartridge is disposed in the housing and has an interior serving as a reservoir for a drug. A button is disposed in the second opening of the shell to be moveable between first and second positions. The button is releasably secured to the shell to be held in its first position. A needle carrier is disposed within the shell and is coupled to the button. A delivery needle is disposed on the needle carrier opposite from the button, wherein in the second position of the plunger the legs engage the button to release it from the shell and wherein in the first position of the button the delivery needle is enclosed with the shell in the second position of the button the delivery needle is exposed from the shell and is in fluid communication with the reservoir.

According to another embodiment of the invention, an injection device is provided. The injection device comprises a housing having a first end defining a first opening. A plunger is received within the first opening of the housing to move between first and second positions. A cartridge is disposed in the housing and has an interior serving as a reservoir for a drug. A delivery needle is disposed within the housing and is in fluid communication with the reservoir via an interruptible fluid channel. A locking mechanism is disposed in the housing. In the first position of the plunger the plunger encloses the delivery needle. In the second position of the plunger the delivery needle is in an injection position and the plunger actuates the locking mechanism whereby when the plunger returns to the first position, the locking mechanism prevents the needle from again being placed in the injection position.

Further objectives and advantages, as well as the structure and function of preferred embodiments will become apparent from a consideration of the description, drawings, and examples.

BRIEF DESCRIPTION OF THE DRAWINGS

The foregoing and other features and advantages of the invention will be apparent from the following, more particular description of a preferred embodiment of the invention, as illustrated in the accompanying drawings wherein like reference numbers generally indicate identical, functionally similar, and/or structurally similar elements.

DETAILED DESCRIPTION OF THE INVENTION

Embodiments of the invention are discussed in detail below. In describing embodiments, specific terminology is employed for the sake of clarity. However, the invention is not intended to be limited to the specific terminology so selected. All references cited herein are incorporated by reference as if each had been individually incorporated.

A preferred embodiment of the invention is discussed in detail below. While specific exemplary embodiments are discussed, it should be understood that this is done for illustration purposes only. A person skilled in the relevant art will recognize that other components and configurations can be used without parting from the spirit and scope of the invention.

Exemplary embodiments of the present invention provide a drug delivery device adapted for automatic infusion of a drug from a pre-filled cartridge. The drug is delivered to a subject from the cartridge by at least one delivery cannula. The cartridge is disposed in a housing of the device. In use, a distal end of the device is pressed against the skin. This action inserts the delivery cannula into the skin while initiating a means for expelling the drug from the cartridge. In one embodiment, a spring forces the drug from the cartridge through the delivery cannula and into the skin. After the drug has been delivered, an indicator may alert the user that the injection process is complete. A safety mechanism is engaged when the device is lifted from the skin to prevent the future exposure of the delivery cannula. The drug delivery device may then be discarded.

Figure 1:
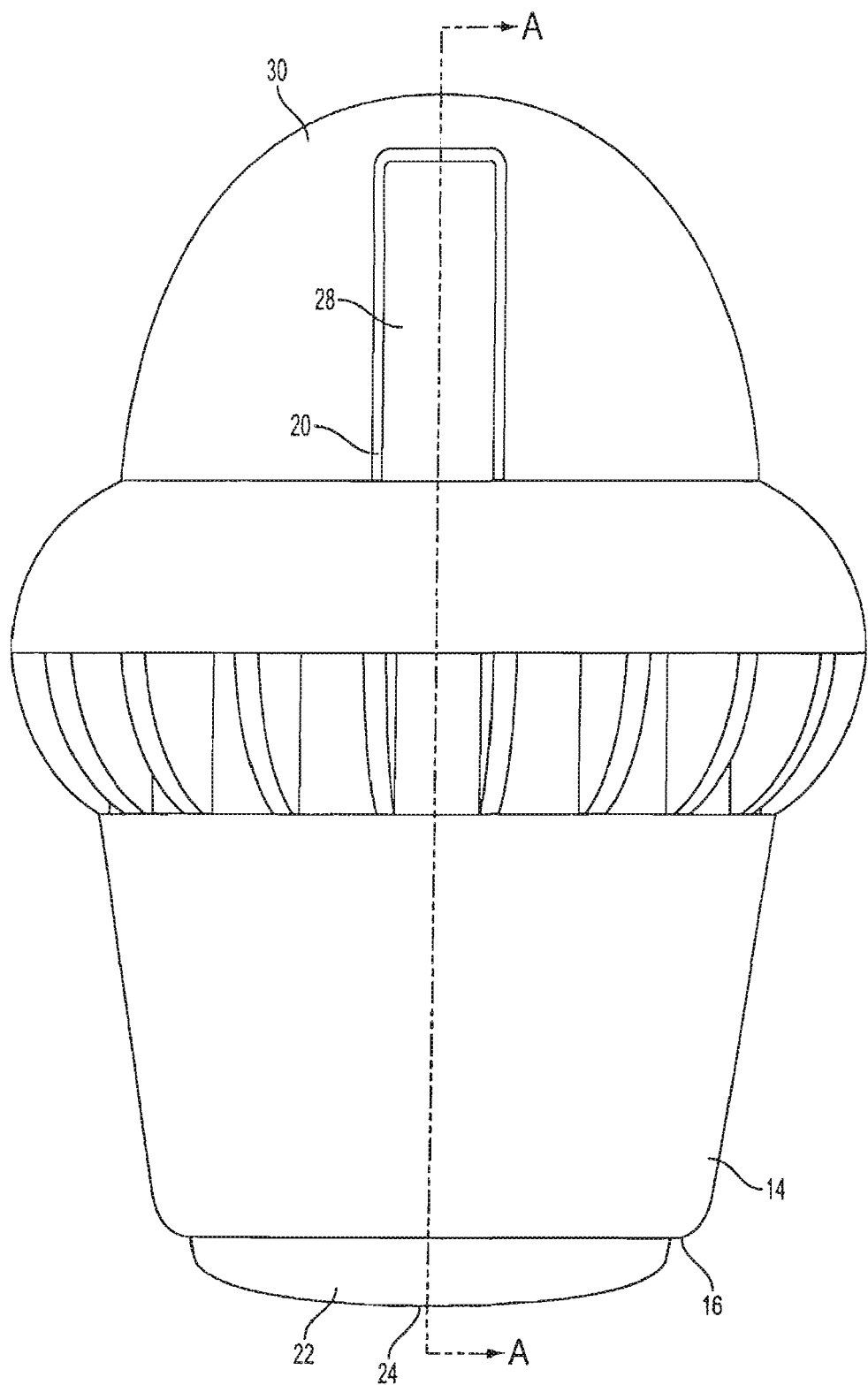
FIG. 1 is a perspective view of a delivery device according to an exemplary embodiment of the present invention.

FIG. 1 illustrates a perspective view of a drug delivery device 10 according to an exemplary embodiment of the present invention. The device includes a housing 12 having a first end 14 defining a first opening 16 and a second end 18 defining a second opening 20. A plunger 22 is received within the first opening 16 of the housing 12. The plunger 22 has a bottom surface 24 that is adapted to be brought into contact with the skin of a subject. The bottom surface 24 of the plunger 22 is exposed through the first opening 16. The bottom surface 24 of the plunger may be flat and carry a layer of pressure sensitive adhesive that allows the device to be affixed to the skin of a patient. The device has a longitudinal axis A-A when the plunger 22 is applied to the skin of a subject.

A vial or cartridge 28 is disposed in the housing 12 along the longitudinal axis A-A. The cartridge 28 has an interior that serves as a reservoir 46 for a drug or other liquid preparation. In the embodiment illustrated, the cartridge 28 is disposed in the second opening 20 of the housing 12 and extends out of the housing. Alternatively, the cartridge can be completely contained within the housing. In use of the device, the plunger 22 is pressed against the skin of the subject. This inserts a delivery needle into the skin of the subject and initiates drug flow. As the drug within the cartridge 28 is expelled, the cartridge 28 moves along the longitudinal axis distally into the housing 12, indicating completion of the drug delivery process. A cap 30 may be provided over the second end 18 of the housing 12 to protect the cartridge 28. The cap may be transparent or include a slot through which the movement of the cartridge 28 can be observed.

Figure 2:
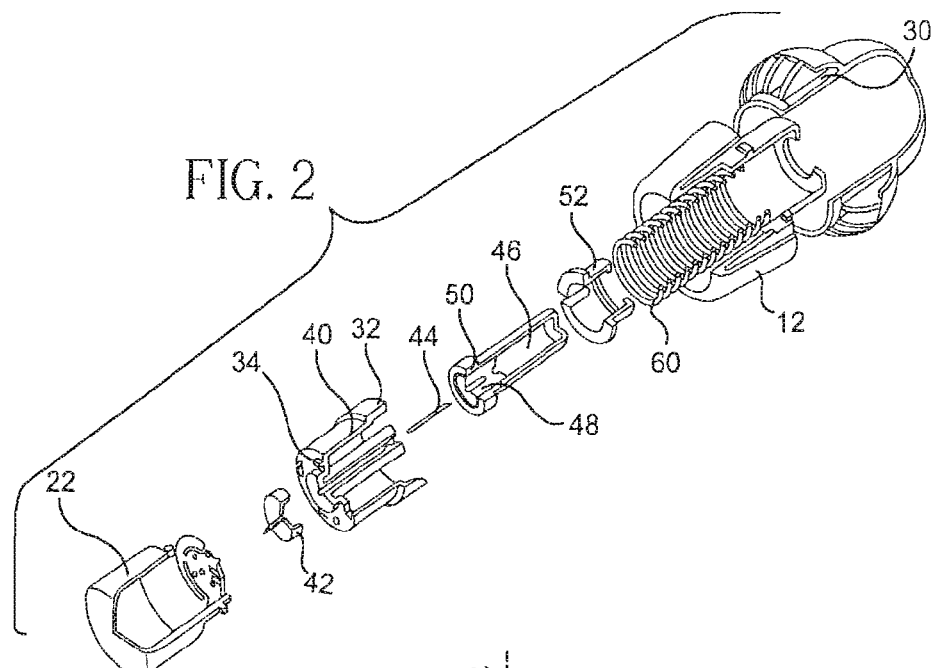
FIG. 2 is an exploded view of the device of FIG. 1.
Figure 3:
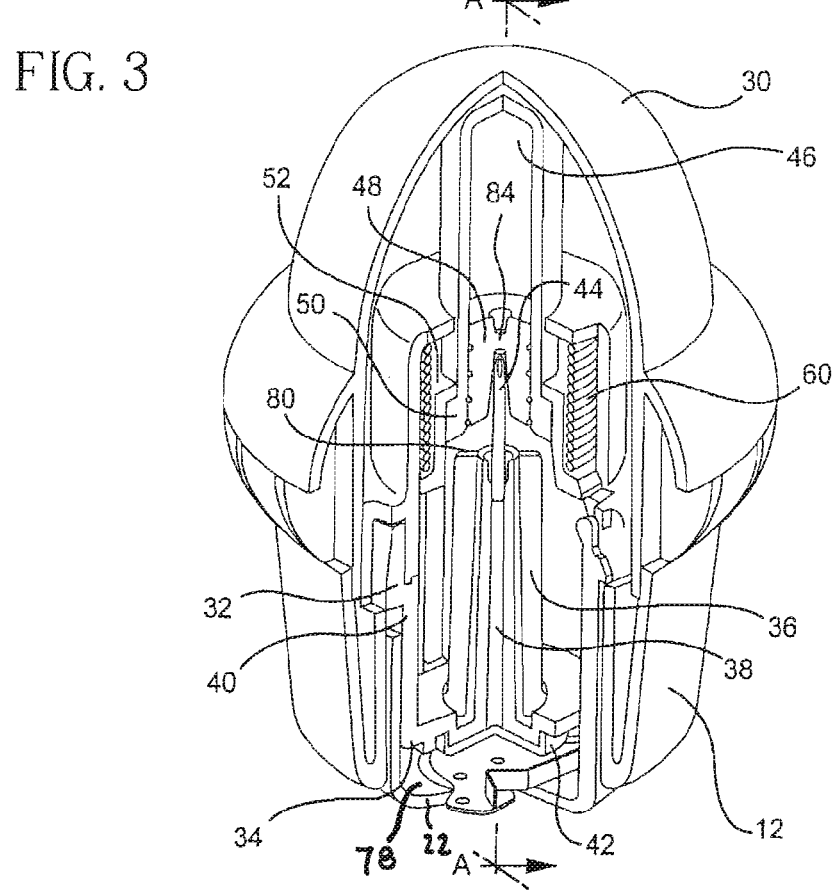
FIG. 3 is a cross-sectional view of the device of FIG. 1 in its first position.

Referring now to FIGS. 2 and 3, the various components comprising an embodiment of the invention are described in more detail. FIG. 2 is an exploded view and FIG. 3 is a cross-section view. A needle carrier 32 is disposed in the housing 12. The needle carrier 32 is preferably fixed in place within the housing 12. A bottom 34 of the needle carrier 32 faces the first end 14 of the housing 12 as shown in FIG. 3. A pedestal 36 extends from the bottom 34 towards the second end 18 of the housing 12. A longitudinal bore 38 extends through the pedestal 36. The longitudinal bore 38 is typically located along the longitudinal axis A-A of the device and extends from one end of the pedestal 36 to the other. An annular surface 40 is arranged around the pedestal 36 with a receiving space defined between the pedestal 36 and the annular surface 40. The annular surface 40 is adapted to hold the needle carrier 32 in place in the housing 12.

A delivery needle 42, which may be a micro-needle array, a single needle or other delivery cannula, is coupled to the needle carrier 32 and is in fluid communication with the longitudinal bore 38. The delivery needle 42 is arranged on a needle hub 34 of the needle carrier 32. The needle hub is cylindrical protrusion from the needle carrier 32. The delivery needle 42 is adapted to be placed in an injection position in which it can penetrate the skin of a user. The length of the delivery needle may be about 0.5 mm to about 5 mm. The delivery needle can be adapted for intradermal, subcutaneous or intramuscular injection can be used. The delivery needle typically has lengths of about 0.5 mm-2 mm for intradermal injection, about 2 mm-3 mm. for subcutaneous injection, and greater than about 3 mm for intramuscular injection. The gauge of the delivery needle is preferably about 30 to about 34 gauge.

A conduit, such as access needle 44, is in fluid communication with the longitudinal bore 38 at the end 80 of the pedestal 36 opposite from the delivery needle 42. The access needle 44 may be arranged in the longitudinal bore 38 such that a fluid path is established between the delivery needle 42 and the access needle 44. The access needle 44 may be a relatively large gauge needle, for example about 25 gauge.

The access needle 44 also forms a fluid path for the drug from the cartridge 28 to the delivery needle 42. As mentioned above, the drug to be delivered is stored in reservoir 46 in the cartridge 28. The cartridge 28 may be cylindrical in shape with its interior defining the reservoir 46. The cartridge 28 has an open end which is sealed by a stopper 48. A rim 50 may be provided on the exterior of the cartridge 28 around the open end. The cartridge 28 is disposed in the housing 12 above the needle carrier 32, towards the second end 18 of the housing 12. The cartridge 28 is movable between first and second positions, the first position being prior to use of the device and the second position being following use of the device. The positions of the cartridge 28 are described in more detail below.

Figure 4:
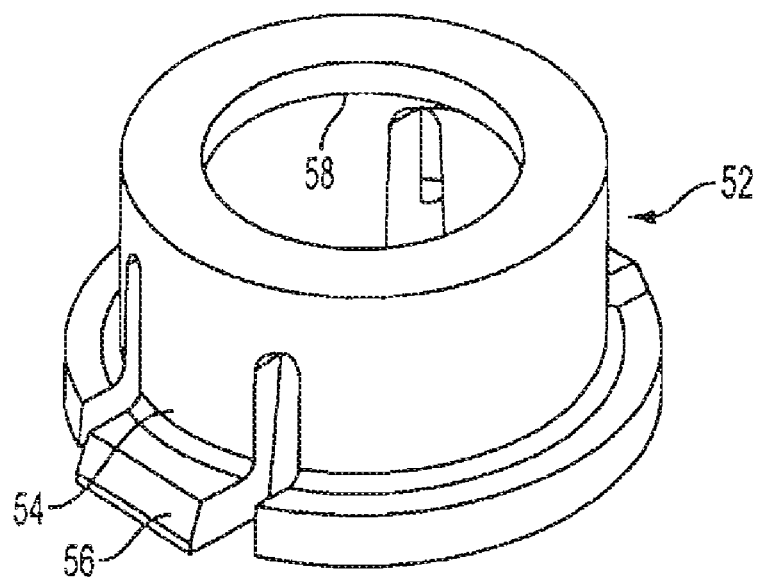
FIG. 4 is a detailed view of a collar according to an exemplary embodiment of the present invention.

A collar 52 may be provided to releasably hold the cartridge 28 in its first position. A detailed view of an example of a collar 52 is shown in FIG. 4. The collar 52 is adapted to fit over an exterior of the cartridge 28. The collar 52 preferably snap-fits over the cartridge 28. Here, the collar 52 is generally cylindrically-shaped with an open center to receive the cartridge 28. At least one retaining latch 54 is provided on the collar 52. The latches 54 include a projecting portion 56 that is received by a corresponding surface of the housing 12. The latches 54 are preferably resilient and are normally biased outward from the collar 52 to engage the housing 12, thereby holding the cartridge 28 in place. The collar 52 is also provided with a mating surface 58 arranged around the periphery of its open center. The mating surface 58 rests against the rim 50 of the cartridge 28 to fit the collar 52 in place around the open end of the cartridge 28. The collar 52 releasably secures the cartridge 28 to housing 12 via the retaining latches 54. The collar 52 and cartridge 28 may be separate elements as described above or formed as an integral unit. In the illustrated embodiment, the collar is formed from an injection-molded polymer. However, the collar 52 may also be formed as a stamped metal piece with three prongs serving as retaining latches.

A means for expelling the drug from the cartridge 28 is also provided. The means for expelling the drug may include a resilient member, a spring, or gas pressure. In the illustrated embodiment, the means for expelling comprises a spring 60. The spring 60 is adapted to move the cartridge 28 from its first position to its second position as is described in more detail below. In the illustrated embodiment, the spring 60 has one end that rests against the collar 52 or is otherwise biased against the cartridge 28 and a second end which rests against the housing 12. The spring 60 is arranged coaxially around the cartridge 28. In the first position of the cartridge 28, the spring 60 is compressed as shown in FIG. 3. The cartridge 28 is held in the first position against the force of the compressed spring 60 via the retaining latches 54. Cap 30 may be provided over the second end 18 of the housing 12 to protect the cartridge 28 from damage or contamination.

Figure 5:
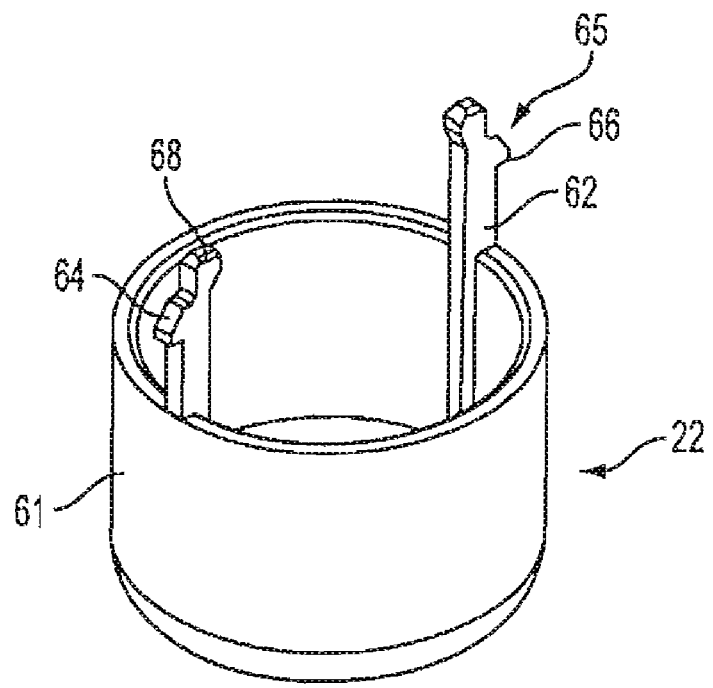
FIG. 5 is a detailed view of a plunger according to an exemplary embodiment of the present invention.

The plunger 22 is slideably received within the first opening of the housing 12 to move into and out of the housing 12 between first and second positions. A detailed view of a plunger 22 according to an exemplary embodiment of the invention is shown in FIG. 5. The plunger 22 has a generally cylindrically shaped body that is hollow and open at both ends. The needle carrier 32 is received within the hollow body such that the plunger 22 is disposed between the needle carrier 32 and the housing 12 as shown in FIG. 3. The bottom surface 24 of the plunger 22 is adapted to be brought into contact with the skin of the subject. At least one prong 62 extends from the body into the housing 12 towards the second end 18 of the housing 12. The needle carrier 32 may be provided with slots (not shown) to receive the prong 62 and allow for its movement. The prong 62 includes a catch 64 and an actuator 68. The catch has a delimiting surface 66. The delimiting surface 66 interacts with the housing 12 to define the first position of the plunger 22 and the needle hub 34 acts as the delimiting surface for proximal movement of the plunger 22, as described in more detail below. The actuator 68 is used to initiate the drug delivery process when the plunger is depressed.

Figure 6:
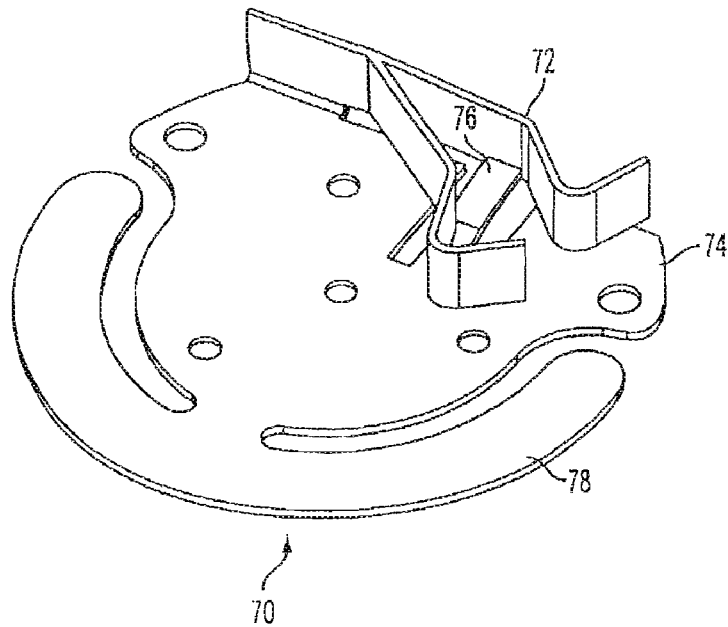
FIG. 6 is a detailed view of a safety interlock according to an exemplary embodiment of the present invention.

The drug delivery device may also be provided with a locking mechanism to prevent accidental needle sticks or re-use of the needle. The locking mechanism may be part of a safety interlock 70 that is illustrated in FIG. 6. The locking mechanism includes a safety spring 72. The safety spring 72 is coupled to a main body 74 of the safety interlock 70. One end of the safety spring 72 is attached at an edge of the main body 74 and the other end of the safety spring 72 is moveable. The safety spring 72 is resilient and has a relaxed position towards the center of the main body 74. A finger 76 is also provided on the main body 74. The finger 76 is flexible and extends upward. As shown in FIG. 6, the finger 76 can hold the safety spring 72 back from its relaxed position, at the edge of the main body 74. In this position, the plunger is free to move to its second position.

The safety interlock 70 may also include a resilient member. The resilient member biases the plunger 22 outward from the housing 12 into its first position. In the illustrated embodiment, the resilient member comprises a wave washer segment 78 coupled to the main body 74. The wave washer segment 78 is biased against the plunger 22. The safety interlock 70 is disposed in the housing 12 between the bottom of the plunger 22 and the delivery needle 42. A space is provided between the safety interlock 70 and the delivery needle 42 as well as between the safety interlock 70 and the annular surface of the plunger 22, when the plunger 22 is in its first position. Thus the safety interlock 70 is essentially free floating in the housing 12. A positioning boss may be provided on the plunger 22 to maintain the safety interlock's position. The main body 74 of the safety interlock 70 includes an opening through which the delivery needle 42 can pass.

Before the device is used, both the plunger 22 and the cartridge 28 are in their first positions and the locking mechanism is held back by the finger 76. FIG. 3 shows the plunger 22 and the cartridge 28 in their first positions. The cartridge 28 in its first position is arranged above the needle carrier 32 and partially extends outside of the housing 12 through the second opening 20. The spring 60 is compressed and arranged coaxially around the cartridge 28 and the collar 52. One end of the spring 60 rests against a surface of the housing 12 around a periphery of the second opening 20. The other end of the spring 60 rests against the collar 52. The collar 52 holds the cartridge 28 in place in its first position via the retaining latches 54.

The reservoir 46 in the cartridge 28 contains a precisely measured dosage of a drug. The stopper 48 is positioned at the open end of the cartridge 28 to seal the drug therein. The cartridge 28 and needle carrier 32 are preferably aligned along the longitudinal axis A-A such that stopper 48 is arranged above the pedestal 36 when the cartridge 28 is in its first position as shown in FIG. 3. Space may be provided between the end surface 80 of the pedestal 36 and the stopper 48 or the end surface of the pedestal 36 may rest against the stopper 48. The stopper 48 may include a central channel for receiving the access needle 44. A barrier 84 blocks the channel preventing the access needle 44 from reaching the drug. The barrier may be inset from the top surface of the stopper 48 as shown in FIG. 3. In the first position of the cartridge 28 the access needle 44 is not yet in fluid communication with the reservoir 46. The access needle 44 may be partially inserted into the stopper 48 or the central channel, but does not completely pierce the stopper 48 or barrier.

The plunger 22 at least partially extends from the first opening of the housing 12 in its first position. The plunger 22 prevents the delivery needle 42 from being accessed from outside the housing 12 when in its first position, as mentioned above. The wave washer 78 biases the plunger 22 into its first position. In the first position of the plunger 22, delimiting surface 66 contacts a retaining surface 84 of the housing 12. The abutment of the delimiting surface 66 and the retaining surface 84 acts against the force of the wave washer 78 to prevent further movement of the plunger 22 from the housing 12. Lower delimiting surface 66 prevents the wave washer 78 from completely expelling the plunger 22 from the housing 12. The location where the retaining surface 84 and delimiting surface 66 contact each other defines the first position of the plunger 22. The first position of the plunger 22 and the safety interlock 70 are selected such that the wave washer 78 is biased against the plunger 22.

Figure 7:
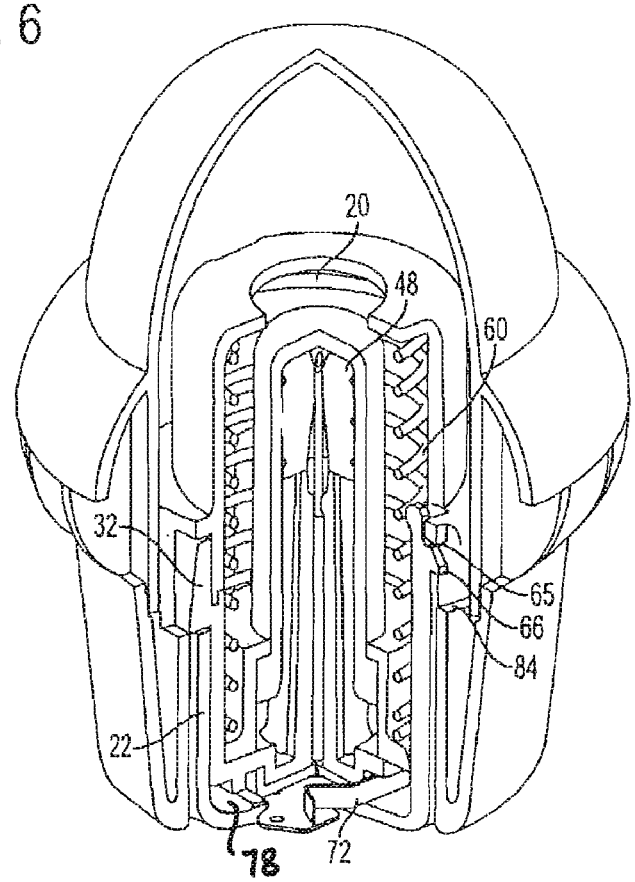
FIG. 7 is a cross-sectional view of the device of FIG. 1 in its second position.

The device is ready for use with the plunger 22 and cartridge 28 in their respective first positions and the locking mechanism retained by finger 76. In use, the device is pressed against an injection site on a user. Upon the pressure against the skin of the user, the plunger 22 acts against the spring force of the wave washer 78 and is depressed into the housing 12. The prong 62 on the plunger 22 moves proximally into the housing 12. The plunger lifts the safety interlock 70 against the needle hub 34 as shown in FIG. 7. When the needle hub 70 engages the safety interlock, the movement of the plunger 22 into the housing 12 is stopped. Also, an end of the plunger 22 may contact the needle carrier 32 as it moves distally into the housing 12 and reaches its second position. A thickness of the plunger 22, a thickness of the safety interlock 70 and the overall length of the needle determine the depth the delivery needle 42 penetrates into the skin.

As the plunger 22 is pressed against the skin of the subject, the plunger 22 lifts the safety interlock 70 against the needle hub 34. The safety interlock 70 is compressed against the needle hub 34 and the needle hub 34 actuates the locking mechanism. In the illustrated embodiment, the finger 76 is depressed by the needle hub 34 and in turn frees the safety spring 72 to move radially inward. The safety spring is temporarily prevented from completely moving inwardly. The safety spring 72 moves over the finger 76 and temporarily rests against the side of the needle hub 34 as shown in FIG. 7.

FIG. 7 illustrates the device with the cartridge 28 and the plunger 22 in their second positions. When the plunger 22 reaches its second position, the delivery needle 42 is in the injection position and is exposed via the opening in bottom surface of the plunger 22. Due to the pressure placed against the device, the delivery needle 42 penetrates the skin of the user. At about the same time, the actuator 68 on the prong 62 engages the retaining latches 54 on the collar 52 to release the cartridge 28 from the housing 12. In the embodiment illustrated, the prong 62 on the plunger 22 moves proximally and the actuator 68 radially compresses the retaining latches 54. The latches 54 are thus released from corresponding surfaces on the housing 12, which allows movement of the cartridge 28. The prong 62 is provided with an engagement surface 65 on a backside of the prong. Surface 62 engages a mating surface on the housing 12 to prevent the prong from spreading as it reaches the latches 54. The mating surface on the housing keeps the prong 62 pressed inward.

As the user continues to hold the device against the skin, the drug is injected through the delivery needle 42 due to the pressure created inside the cartridge 28 by the compression spring 60 reacting against the collar 52. The spring 60 acts against the collar 52 to move the cartridge 28 towards the first end 14 of the housing 12. The end surface 80 of the pedestal 36 engages the stopper 48. The pedestal 36 is adapted to be received within the interior of the cartridge 28. Accordingly, the end surface 80 of the pedestal 36 extends transverse to the longitudinal axis of the device an amount less than the interior diameter of the cartridge 28. The receiving space around the pedestal 36 should be large enough to accommodate the collar 52, spring 60 and cartridge 28 as the pedestal 36 enters the interior of the cartridge 28.

As the spring 60 moves the cartridge 28, the access needle 44 pierces the barrier of the stopper 48 and enters into fluid communication with the reservoir 46 and the interior of the cartridge 28. Once the stopper 48 is punctured, the bore in the access needle 44 forms an escape path for the drug. The end surface 80 of the pedestal 36 holds the stopper 48 in place. Thus, the stopper 48 is prevented from moving along with the cartridge 28 as the cartridge 28 is driven by the spring 60. The stopper 48 acts as a piston and creates a pressure inside the cartridge 28. This pressure forces the drug contained within the cartridge 28 through the access needle 44 into the delivery needle 42. The action of the cartridge 28 being driven down over the stopper 48 thus injects the drug into the user. The drug is pumped through the access needle 44 and a fluid channel defined by the longitudinal bore 38 to the delivery needle 42 as the stopper 48 is pushed up into the reservoir 46 as a result of the spring 60 pushing the collar 52 and cartridge 28 towards the first end 14 of the housing 12. As the drug is emptied from the cartridge 28, the cartridge 28 moves distally into the housing 12. The spring 60 moves the cartridge 28 into the housing 12 until the collar 52 or cartridge 28 is stopped by a surface of the needle carrier 32 or until the stopper 48 reaches the closed end of the cartridge 28 as shown in FIG. 7.

Figure 8:
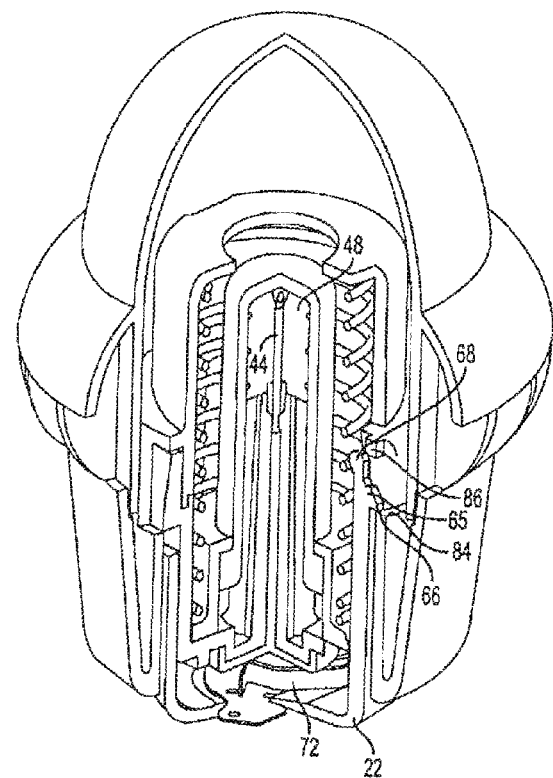
FIG. 8 is a detailed view of a safety interlock in its activated position according to an exemplary embodiment of the present invention.

Once the injection is complete, the device is lifted from the skin of the subject. Without the pressure from the skin, the wave washer 78 forces the plunger 22 distally back to its first position. In turn, the safety interlock 70 and the locking mechanism also move distally away from the delivery needle 42. As the safety spring 72 is free from the needle hub 34, it moves radially until it is in its relaxed state distal to the needle hub 34 as shown in FIG. 8. In this position, the locking mechanism blocks the plunger 22 from moving into the housing 12 and the plunger 22 cannot be depressed proximally. Accordingly, when the plunger 22 moves from its second position to its first position, the locking mechanism is activated to prevent the delivery needle 42 from being exposed and to prevent accidental needle sticks.

Figure 9:
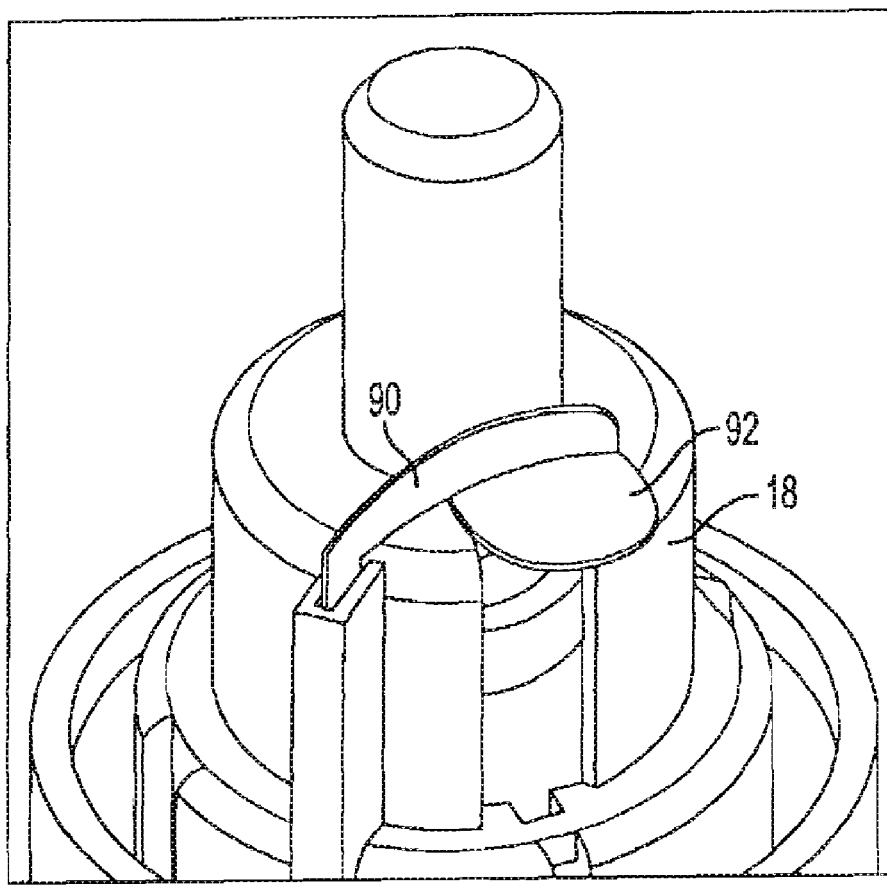
FIG. 9 illustrates an indicator according to an exemplary embodiment of the present invention.

In a further embodiment of the present invention, an indicator is provided to indicate when the injection process is complete. The indicator may comprise a resilient member 90 arranged on the outside of the second end 18 of the housing 12 as shown in FIG. 9. One end of the resilient member 90 is attached to the housing 12. A second end of the resilient member 90 rests against the cartridge 28 when the cartridge 28 is in its first position protruding from the second opening 20. The resilient member 90 has a relaxed position towards the longitudinal axis of the housing 12 and is biased against the cartridge 28. As described above, the cartridge 28 moves distally into the housing 12 as the drug is expelled from the cartridge 28. When the injection of the dose is complete, the cartridge 28 is completely within the housing 12. The resilient member 90 is now free to move to its relaxed state towards the longitudinal axis of the device. A flag portion 92 of the resilient member 90 moves over the second opening 20 to indicate that the delivery of the drug dosage is complete. Also, cap 30 for the device may be transparent to allow the user to observe when the injection of the drug is complete.

Figure 10:
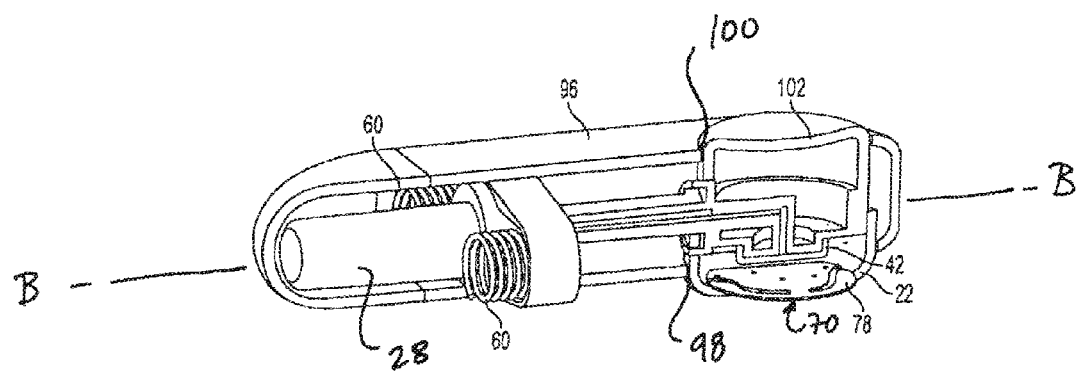
FIG. 10 is a cross-sectional view of a device according to another exemplary embodiment of the present invention.

FIG. 10 illustrates another embodiment of the present invention. In this embodiment, the injection device includes a shell 96 having a longitudinal axis B-B. The shell 96 defines first and second openings 98, 100 that are arranged on opposite sides of the longitudinal axis from each other. The plunger 22 is slideably received within the first opening 98 of the shell 96 to move between first and second positions. The first position of the plunger 22 is similar to that described above. In this embodiment, the plunger 22 moves between its first and second positions in a direction perpendicular to the longitudinal axis of the device.

A button 102 is disposed in the second opening 100 of the shell 96. The button 102 is moveable between first and second positions. The button 102 is releasably secured in its first position to the shell 96. A releasable latch may be provided on the button to secure it in its first position. The needle carrier 32 is disposed within the shell 96 and defines a fluid channel. The needle carrier 32 is arranged in between the button 102 and the plunger 22. Preferably, the button 102 is coupled to the needle carrier 32. The delivery needle 42 is disposed on the needle carrier 32 on the side opposite from the button 102 to be in fluid communication with the fluid channel. Preferably the button 102, needle carrier 32 and delivery needle 42 are formed as an integral unit. The safety interlock 70 is disposed between the delivery needle 42 and the plunger 22. Access needle 44 is disposed in fluid communication with the fluid channel.

Cartridge 28 with stopper 48 is disposed along the longitudinal axis of the device and is moveable between first and second positions. Collar 52 and spring 60 similar to that described above are also disposed in the shell. In this embodiment, the cartridge 28 moves along the longitudinal axis of the device in a direction perpendicular to the direction of movement of the button and the plunger 22. Two springs 60 are provided to move the cartridge 28 from its first position to its second position. The components of this embodiment may be slightly modified from that described above to accommodate the different shape of the device.

The relationship of the components in their first position is also similar to the first embodiment described above. When the plunger 22, cartridge 28, and button 102 are in their respective first positions, the device is ready for use. In operation of the second embodiment, the user pushes the device against their skin. A pressure sensitive adhesive layer provided on the bottom surface of the plunger 22 adheres the device to the skin. By pressing the device against the skin, the plunger 22 is moved against the force of the resilient member and moves distally into the shell 96. This action arms the device by releasing the button 102 from the shell 96. The button 102 can be released from the shell 96 by an activator on the plunger 22 similar to that described above. Here, the activator engages the releasable latches on the button 102 and compress them radially to release the button 102 from the shell 96. This action arms the device for injection.

Next, the button 102 is depressed by the user to initiate the injection process. When the button 102 is pressed, the button 102, needle carrier 32, and delivery needle 42 move distally and press the delivery needle 42 into the skin. Nearly simultaneously, the movement of the button 102 to its second position releases the latch holding the cartridge 28 to the shell, allowing the cartridge 28 to be forced against the needle carrier 32 under the pressure of the spring 60. Additionally, as the needle hub 34 and needle carrier 32 press against the safety interlock 70, the locking mechanism is activated, freeing the safety spring as described above and allowing it to move radially and rest temporarily against the needle hub 34, as described above.

As the drug is delivered into the skin, the cartridge 28 moves along the longitudinal axis to its second position. Upon completion of the delivery of the dose, the device is removed from the skin. As described above, the plunger 22 moves distally under pressure from the wave washer segment. This allows the locking mechanism to move radially and prevent the plunger 22 from being depressed to again expose the delivery needle 42.

Accordingly, a drug delivery device that is capable of delivering a pre-set dosage of drug to a subject is provided. The device is suitable for use in self-administration by patients (including young patients and elderly patients) and does not require the patient to consciously insert a needle into the skin. A safety mechanism is provided to prevent re-use of the needle. The safety mechanism can be modified to accommodate different needle lengths. In the embodiment described above, the height the finger 72 extends from the main body can be changed for different needle lengths.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:
1. An injection device, comprising:
a housing having a first end defining a first opening;
a plunger received within the first opening of the housing to move between first and second positions;
a cartridge disposed in the housing and having an interior serving as a reservoir for a drug;
a delivery needle disposed within the housing and in fluid communication with the reservoir via an interruptible fluid channel;
a locking mechanism disposed in the housing, said locking mechanism including a first resilient member having a relaxed position towards a center of the first opening;

a latch configured for holding the first resilient member clear of the first opening to enable the delivery needle to be placed into an injection position; and a needle hub carrying the delivery needle, wherein, in the first position of the plunger, the delivery needle is enclosed by the plunger, wherein, in the second position of the plunger, the latch is released by the needle hub with the first resilient member resting against a side of the needle hub while the delivery needle is in the injection position, and, wherein when the plunger returns to the first position from the second position, the locking mechanism prevents the needle from being placed in the injection position.

2. The device of claim 1, further comprising an interlock including a second resilient member biasing the plunger to at least partially extend out of the first opening.

3. The device of claim 2, wherein the first resilient member is connected to the interlock.

4. The device of claim 1, wherein in the injection position the delivery needle is exposed via the first opening.

5. The device of claim 1, wherein when the plunger returns to the first position, the first resilient member moves towards the center of the first opening and prevents the delivery needle from being placed in the injection position.

6. The device of claim 1, wherein the plunger further comprises a bottom surface adapted to be brought into contact with the skin of a subject.

7. The device of claim 1, further comprising means for expelling the drug from the reservoir.

8. The device of claim 7, wherein the means for expelling comprises a spring.

9. The device of claim 1, further comprising an indicator for indicating when the injection is complete.

10. The device of claim 1, further comprising a needle carrier disposed in the housing, the delivery needle being attached to the needle carrier via the needle hub.

11. The device of claim 10, wherein the needle carrier is fixed in the housing.

12. The device of claim 10, wherein a portion of the interruptible fluid channel comprises a longitudinal bore through the needle carrier, the delivery needle being disposed at one end of the bore.

13. The device of claim 12, further comprising an access needle disposed at another end of the bore.

14. A medical device, comprising:

a housing extending along a longitudinal axis having a first end defining a first opening;

a plunger received within the first opening of the housing to move between first and second positions;

a needle a needle carrier, the needle being attached to the needle carrier; and a locking mechanism disposed in the housing, said locking mechanism including a first resilient member having a relaxed position towards a center of the first opening, wherein, in the first position of the plunger, the needle is enclosed by the plunger, wherein, in the second position of the plunger, the first resilient member being displaced from the relaxed position so as to allow the needle to be in an exposed position, and, wherein, when the plunger returns to the first position from the second position, the first resilient member moves about an axis parallel to said longitudinal axis towards the relaxed position in between the first opening and portions of the needle carrier such that the first resilient member inhibits movement of the plunger to the second position whereby the locking mechanism prevents the needle from being placed in the exposed position.

15. The device of claim 14, further comprising an interlock including a second resilient member biasing the plunger to at least partially extend out of the first opening.

16. The device of claim 15, wherein the first resilient member is connected to the interlock.

17. The device of claim 14, wherein in the exposed position the needle is exposed via the first opening.

18. The device of claim 16, further comprising a latch configured for holding the first resilient member in the state displaced from the relaxed state clear of the first opening to enable the needle to be placed to the exposed position.

19. The device of claim 18, wherein the latch is released from holding the first resilient member upon movement of the plunger to the second position from the first position.

* * * * *